United States Patent [19]

Wieser et al.

[11] 4,308,383

[45] Dec. 29, 1981

[54] N-(3-(1'-3"-OXAPENTAME-THYLENEAMINO-ETHYLIDENEAMINO)-2,4,6-TRIIODOBENZOYL)-β-AMINO-α-METHYLPROPIONITRILE

[75] Inventors: Josef Wieser; Josef Krieger, both of Linz, Austria

[73] Assignee: Chemie Linz Aktiengesellschaft, Austria

[21] Appl. No.: 218,741

[22] Filed: Dec. 22, 1980

[30] Foreign Application Priority Data

Jan. 4, 1980 [DE] Fed. Rep. of Germany ....... 3000209

[51] Int. Cl.³ ............................................. C07D 295/14
[52] U.S. Cl. ..................................... 544/163; 544/165
[58] Field of Search ........................................... 544/163

[56] References Cited

U.S. PATENT DOCUMENTS 3,890,318  6/1975  Obendor et al. ...................... 544/86

Primary Examiner—Henry R. Jiles
Assistant Examiner—R. W. Ramsuer
Attorney, Agent, or Firm—Wenderoth, Lind & Ponack

[57] ABSTRACT

The present invention relates to the novel compound N-[3-(1'-3"-Oxapentamethyleneamino-ethylideneamino)-2,4,6-triiodobenzoyl]-β-amino-α-methylpropionitrile which due to the sparing solubility in water, can be purified readily in a simple manner and can be used for the preparation of the known active compound for agents for peroral rapid cholecystography N-[3-(1'-3"-oxapentamethyleneamino-ethylideneamino)-2,4,6-triiodobenzoyl]-β-amino-α-methyl propionic acid.

1 Claim, No Drawings

N-(3-(1'-3''-OXAPENTAMETHYLENEAMINO-ETHYLIDENEAMINO)-2,4,6-TRIIODOBENZOYL)-β-AMINO-α-METHYLPROPIONITRILE

The present invention relates to N-[3-(1',3''-oxapentamethyleneamino-ethylideneamino)-2,4,6-triiodobenzoyl]-β-amino-α-methylpropionitrile, which is a novel compound, and its use for the preparation of N-[3-(1'-3''-oxapentamethyleneamino-ethylideneamino)-2,4,6-triiodobenzoyl]-β-amino-α-methylpropionic acid, which is known as an active compound in agents for peroral rapid cholecystography.

It is known, from U.S. Pat. No. 3,890,318, that derivatives of 2,4,6-triiodobenzoylaminoalkanecarboxylic acids which carry a substituted amidino group in the 3-position of the benzene nucleus are X-ray contrast media which are used for visualisation of the gallbladder and are particularly distinguished by their ease of absorption and their rapid elimination from the body. Amongst these compounds, N-[3-(1'-3''-oxapentamethyleneamino-ethylideneamino)-2,4,6-triiodobenzoyl[-β-amino-α-methylpropionic acid (iomorinic acid) of the formula I:

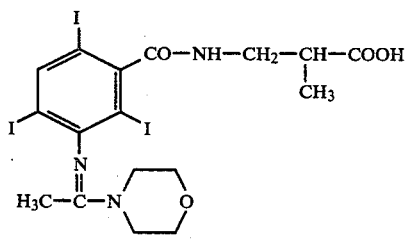

has achieved particular importance and is used as a so-called rapid cholecystography agent. After peroral administration of this compound, preferably in the form of the Na salt, it is possible to obtain photographs of the bile ducts within 60–90 minutes and pictures of the gallbladder within 5 hours, so that it is possible for the agent to be taken and the investigation to be carried out in one day.

According to U.S. Pat. No. 3,890,318 in order to prepare the compound of formula I, 3-amino-2,4,6-triiodobenzoyl chloride is reacted with N-acetylmorpholine and phosphorus oxychloride in chloroform by boiling, and the resulting acid chloride, containing the amidino group which has been formed, is isolated as the salt. After liberating the base, this can then be converted into the compound of the formula I by reaction with β-amino-α-methylpropionic acid esters, also under the action of heat, and subsequent saponification.

This process has the disadvantage that, in the reaction of 3-amino-2,4,6-triiodobenzoyl chloride with acetylmorpholine, by-products which are insoluble in acid and also, as another by-product, the morpholide of 3-(1'-3''-oxapentamethyleneamino-ethylideneamino)-2,4,6-triiodobenzoic acid are formed. These impurities can only be separated off after the preparation of the end product, and their separation is very difficult because the acid of the formula I crystallizes poorly or not at all in the impure form and the purification is very wasteful and necessitates multiple evaporation of mother liquors.

The U.S. patent specification mentioned also gives the reaction of N-(3-amino-2,4,6-triiodobenzoyl)-amino-alkanecarboxylic acid alkyl esters with N-acetylmorpholine and phosphorus oxychloride, likewise whilst boiling under reflux, as another process variant. The morpholide formation can indeed by avoided in this procedure, but the reaction nevertheless does not proceed uniformly and in this case also, by-products which are insoluble in acid are formed. Most of these can indeed be separated off by acidifying the mixture to pH 1-1.5, but certain amounts of these by-products remain in the product and make purification thereof very difficult.

Finally, it is furthermore possible, according to U.S. Pat. No. 3,890,318, to carry out the preparation of the compound of the formula I at room temperature by reaction of N-(3-acetylamino-2,4,6-triiodobenzoyl)-β-amino-αmethylpropionic acid methyl ester with morpholine in the presence of phosphorus pentachloride, but still more by-products are formed in this reaction procedure, so that the yield of pure product is even lower and the purification is even more troublesome than in the case of the other known processes.

A compound which exhibits a good tendency to crystallization and, because of its good solubility and stability in dilute aqueous acids and the sparing solubility of the base in water, can be purified very readily and in a simple manner, could now be found in the new nitrile of the compound of the formula I, which has the formula II:

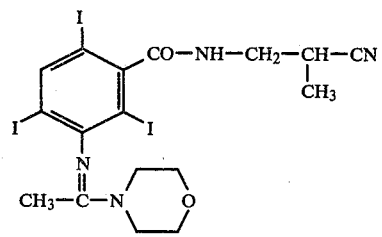

Although this compound can thus unhesitatingly be reprecipitated several times for purification processes, it can, surprisingly, be hydrolysed either with strong acids or in alkaline solution to give the acid of the formula I without the amidino group being attacked, with the formation of harmful impurities, or without iodine being split off. The discovery of this new substance has thus opened a new and advantageous route for the preparation of the compound of the formula I, since, when the pure nitrile of the formula II is subjected to hydrolysis, the acid of the formula I is obtained in such a pure form that at most one simple recrystallization, for example from methanol, which can be carried out without noticeable losses, is sufficient to obtain the acid in a purity which can be used for pharmaceutical administration. Since the wasteful purification of the acid is thus eliminated, and furthermore both the preparation of the nitrile of the formula II and its saponification take place with very good yields, it is therefore also possible to prepare iomorinic acid of the formula I in a considerably higher yield than was hitherto the case.

The present invention accordingly relates to the new nitrile, of iomorinic acid, of the formula II, and its use for the preparation of iomorinic acid of the formula I by hydrolysis.

For the preparation of the nitrile of the formula II, N-(3-amino-2,4,6-triiodobenzoyl)-β-amino-α-methyl-propionitrile can be reacted with N-acetylmorpholine in an inert reaction medium in the presence of phosphorus oxychloride. By treating the resulting reaction mixture with water, before or during evaporation of the solvent used, an acid aqueous solution containing the nitrile of the formula II in the form of a salt is obtained. Any by-products present which are insoluble in acid can then be separated off in the form of a solid in a simple manner, for example by filtration. If the clear acid solution is then neutralised and a pH value of at least 8 is established, the sparingly soluble nitrile separates out, either directly in crystalline form or as an oil which very rapidly crystallizes completely, and can thus easily be isolated in solid form.

However, it is also possible to obtain the nitrile of the formula II starting from 3-(1'-3''-oxapentamethyleneamino-ethylideneamino)-2,4,6-triiodobenzoyl chloride, by reaction with β-aminoisobutyronitrile, likewise in an inert solvent. In this case, after evaporating off the solvent, the reaction product must first be dissolved by treatment with dilute acid and then precipitated by rendering the solution alkaline.

In carrying out the reaction of N-(3-amino-2,4,6-triiodobenzoyl)-β-amino-α-methylpropionitrile with N-acetylmorpholine and phosphorus oxychloride, which is the preferred process variant, it is expedient to employ both the N-acetylmorpholine and the POCl₃ in excess compared with the nitrile. 1.5–3 mols of N-acetylmorpholine and 2–6 mols of phosphorus oxychloride are appropriately employed per mol of the nitrile. This excess of the two reactants suppresses the formation of by-products and increases the yield, better results being achieved, within the limits indicated, if at least one of the two starting materials is employed in an amount corresponding to the upper region of the range indicated. Less than 5% of by-products, and yields of nitrile of the formula II greater than 95% are obtained if 3 mols of N-acetylmorpholine and 2–6 mols of POCl₃ are employed per mol of N-(3-amino-2,4,6-triiodobenzoyl)-β-amino-α-methylpropionitrile. In contrast, if only 2 mols of N-acetylmorpholine are used, 6 mols of POCl₃ are required per mol of N-(3-amino-2,4,6-triiodobenzoyl)-β-amino-α-methylpropionitrile in order to achieve optimum results. The best results are obtained with a molar ratio of 1:3:6.

The reaction temperature is preferably kept as low as possible, and in particular in the range between 0° C. and about 20° C. It is particularly favourable to adjust the temperature to about 0° C. when the reactants are mixed together, and to allow the temperature to rise to about 20° C. only in order to bring the reaction to completion. Since the reaction is exothermic, the mixture must be cooled. However, it is also possible to allow the reaction to go to completion at a higher temperature, for example at the boiling point of the reaction mixture, especially if shorter reaction times are desired.

The fact that by-products are also formed, in addition to the nitrile of the formula II, indeed has an effect on the yield, but is of no significance for the success of the process or for the purity of the end product of the formula I. This is because, on the basis of its solubility characteristics, the nitrile of the formula II can be purified in an excellent manner. This means that even when the process is carried out under conditions under which more than 5% of by-products are obtained, purification of the nitrile presents no difficulties and the purity of the end product of the formula I is thus nevertheless satisfactory.

The reaction of N-(3-amino-2,4,6-triiodobenzoyl)-β-amino-α-methylpropionitrile with N-acetylmorpholine and POCl₃ is carried out in an inert reaction medium, and it is expedient to use an inert organic solvent. Since the nitrile used as the starting material is scarecely soluble in the customary organic solvents, the reaction is in most cases carried out in solvents in which the complex which forms from N-acetylmorpholine and phosphorus oxychloride is indeed soluble, but the nitrile is insoluble. Such solvents are, for example, dioxane, tetrahydrofuran, acetonitrile and chlorinated hydrocarbons, such as chloroform or methylene chloride. In spite of the fact that the reaction is carried out in a heterogeneous phase system, the yield is surprisingly very good.

The solubility of the complex of acetylmorpholine and POCl₃ is moreover no prerequisite at all for the success of the process according to the invention. The reaction also proceeds smoothly in those organic solvents, such as aromatic hydrocarbons, in particular toluene, in which the complex of acetylmorpholine and POCl₃ is also insoluble and only suspended therein. The reaction can also be carried out in excess POCl₃ as the solvent. It is expedient also to purify, by adding active charcoal, the acid solution formed when the reaction product is taken up in water. The base of the formula II is then precipitated by rendering the solution alkaline with any water-soluble base which is sufficiently alkaline to ensure that a pH value of at least 8 is achieved. Ammonia is preferably used. If more by-products are present, a second purification can be carried out without difficulty or losses, by dissolving the nitrile of the formula II once more in dilute acid, if necessary treating the solution once more with active charcoal, and precipitating the nitrile again by rendering the solution alkaline.

The second process variant, that is to say the reaction of the acid chloride, in which the amidino group has already been formed, with β-aminoisobutyronitrile, is also likewise carried out in an inert solvent, such as dioxane, chloroform or tetrahydrofuran, it being expedient to warm the mixture. In this case also, the by-products which are insoluble in acid can easily be separated off as a result of the advantageous properties of the nitrile of the formula II. In this case also, purification is carried out, if necessary, by repeatedly dissolving the product in acid, treating the solution with active charcoal and precipitating the nitrile with alkalis, preferably ammonia.

Surprisingly, the saponification of the nitrile of the formula II obtained in a pure form in this manner proceeds entirely smoothly. It can be carried out by treatment with concentrated inorganic acids, such as hydrochloric acid or sulphuric acid. However, it can also be carried out with the aid of alkaline agents, for example with alcoholic-aqueous alkali metal hydroxide solutions, such as NaOH or KOH. Finally, however, it is also possible first to prepare the corresponding imidoester by the action of acids in an alcoholic medium, for example with methanolic hydrochloric acid, and to split this ester by treatment with water. The free compound of the formula I, which is amphoteric in character, is best precipitated from the saponification solution at the isolectric point, whereupon it is obtained in pure form in almost quantitative yield.

The N-(3-amino-2,4,6-triiodobenzoyl)-β-amino-α-methylpropionitrile required as the starting material can be obtained in yields of over 90% in a simple manner, by acylating β-aminoisobutyronitrile with 3-amino-2,4,6-triiodobenzoyl chloride. β-Aminoisobutyronitrile is likewise prepared in a simple manner, by addition of ammonia onto methacrylonitrile, and can easily be obtained in a pure form by distillation.

EXAMPLE 1

77.4 g (0.6 mol) of N-acetylmorpholine are added to 183.6 g (1.2 mols) of phosphorus oxychloride in 500 ml of chloroform at a temperature of 0° C. During this addition, the temperature rises to about 8° C., in spite of further cooling. After the temperature has fallen to 0° C. again, 116.2 g (0.2 mol) of N-(3-amino-2,4,6-triiodobenzoyl)-β-amino-α-methylpropionitrile are added and the suspension is then stirred, without further cooling.

After 40 hours, the chloroform suspension is poured into 800 ml of water, and in particular at a rate such that the chloroform distils off continuously and a clear aqueous phase is formed. In order to drive off last residues of chloroform, the aqueous solution is subsequently boiled up for a short time. It is then cooled and filtered with charcoal and the acid solution is first brought to pH 6 with 40% strength aqueous sodium hydroxide solution and then rendered alkaline with concentrated aqueous ammonia. The nitrile of the formula II which separates out, partly in the form of an oil, becomes solid and filterable when the aqueous-ammoniacal solution is warmed to 85° C. and stirred vigorously for a short time. The product is filtered off and dissolved once more in 1.2 l of water containing 0.4 mol of hydrochloric acid and the solution is treated with charcoal and rendered alkaline with ammonia, as described above, and the product precipitated.

137 g of N-[3-(1'-3''-oxapentamethyleneaminoethylideneamino)-2,4,6-triiodobenzoyl]-β-amino-α-methylpropionitrile of melting point 129°–130° C., that is to say 98.9% of theory, are obtained.

The N-(3-amino-2,4,6-triiodobenzoyl)-β-amino-α-methylpropionitrile required as the starting material is prepared as follows:

106.6 g (0.2 mol) of 3-amino-2,4,6-triiodoaminobenzoyl chloride in 500 ml of chloroform are boiled under reflux with 17.6 g of β-aminoisobutyronitrile and 21.2 g of triethylamine for several hours. The N-(3-amino-2,4,6-triiodobenzoyl)-β-amino-α-methylpropionitrile already starts to crystallize out during heating. In order to bring the crystallization to completion, 200 ml of chloroform are distilled off from the reaction mixture and the mixture is then left to stand at room temperature. After filtration, 108.4 g (93.3%) of the nitrile are obtained. After washing the chloroform mother liquor with water and then concentrating it to 40 ml, a further 6.3 g (5.4%) are obtained. Melting point: 187° C.

EXAMPLE 2

183.6 g (1.2 mols) of phosphorus oxychloride and 77.4 g (0.6 mol) of N-acetylmorpholine are introduced into 500 ml of dioxane at 0° C. and a solution of 116.2 g (0.2 mol) of N-(3-amino-2,4,6-triiodobenzoyl)-β-amino-α-methylpropionitrile in 500 ml of dioxane is then added.

After stirring the mixture overnight, the dioxane is distilled off in vacuo, the residue is taken up in about 1 l of water, the aqueous mixture is filtered over charcoal and the N-[3-(1'-2''-oxapentamethyleneaminoethylideneamino)-2,4,6-triiodobenzoyl]-β-amino-α-methylpropionitrile is precipitated at pH 8.5 by adding ammonia. After filtration, the still moist product is taken up in 1.2 l of 1 N HCl and the mixture is filtered over charcoal. The nitrile is precipitated again from the filtrate, which is now clear, with alkali and is now filtered off. 121 g (87.5% of theory) of N-[3](1'-3''-oxapentamethyleneamino-ethylideneamino)-2,4,6-triiodobenzoyl]-β-amino-α-methylpropionitrile of melting point: 129°–130° C. are obtained.

EXAMPLE 3

19 g of N-acetylmorpholine are added to 250 ml of phosphorus oxychloride at 0° C. In spite of cooling, the temperature thereby rises to 10° C. After 5 minutes, 29 g of N-(3-amino-2,4,6-triiodobenzoyl)-β-amino-α-methylpropionitrile are added at 5° C., whilst further cooling and whilst stirring. Stirring is continued overnight at 20° C., whereupon an almost clear solution is formed.

For working up, the phosphorus oxychloride is as far as possible distilled off in vacuo, the evaporation residue is dissolved in 150 ml of chloroform and the solution is poured into 300 ml of water. The mixture is then further worked up as described in Example 1.

33 g (95.4% of theory) of N-[3-(1'-3''-oxapentamethyleneamino-ethylideneamino)-2,4,6-triiodobenzoyl]-β-amino-α-methylpropionitrile of melting point: 129°–130° C. are obtained.

EXAMPLE 4

19.4 g of N-acetylmorpholine are added to 46 g of phosphorus oxychloride in 200 ml of toluene at 0° C., whilst cooling. After a short time, a white precipitate forms in the solution. 29 g of N-(3-amino-2,4,6-triiodobenzoyl)-β-amino-α-methylpropionitrile are then added, whilst stirring, and stirring is continued for 40 hours at 20° C. The oily reaction product thereby formed is taken up in 400 ml of water and the slightly turbid solution is filtered over charcoal. The N-[3-(1'-3''-oxapentamethyleneamino-ethylideneamino)-2,4,6-triiodobenzoyl]-β-amino-α-methylpropionitrile is precipitated from the clear acid filtrate by adjusting the pH value to 8. 33.2 g are obtained, that is to say 96% of theory. Melting point: 129°–130° C.

EXAMPLE 5

183.6 g (1.2 mols) of phosphorus oxychloride are mixed with 77.4 g (0.6 mol) of N-acetylmorpholine and 116.2 g (0.2 mol) of N-(3-amino-2,4,6-triiodobenzoyl)-β-amino-α-methylpropionitrile at a temperature of 0° C. as described in Example 1, and the mixture is then boiled under reflux for 18 hours. Working up is carried out as described in Example 1.

121.3 g of N-[3-(1'-2''-oxapentamethyleneamino-ethylideneamino)-2,4,6-triiodobenzoyl]-β-amino-α-methylpropionitrile, that is to say 87.6% of theory, are obtained. Melting point: 129°–130° C.

EXAMPLE 6

34 g of 3-(1'-3''-oxapentamethyleneamino-ethylideneamino)-2,4,6-triiodobenzoyl chloride hydrochloride (prepared according to the instructions in U.S. Pat. No. 3,890,318) are suspended in chloroform. The base is liberated by adding triethylamine, after which 5 g of β-aminoisobutyronitrile are added and the mixture is boiled under reflux for 3 hours. The chloroform solution thus obtained is then evaporated in vacuo, the oily residue is taken up in 4 N hydrochloric acid, the mixture is treated with active charcoal and the active charcoal is filtered off. The acid filtrate is then brought to pH 6 by adding 40% strength NaOH, and the pH value is then adjusted to 8.5 with concentrated aqueous ammonia. The precipitate which has thereby separated out is left to stand at 60° C. for some time and is then filtered off and dried. 34.5 g of N-[3-(1'-3''-oxapentamethyleneamino-ethylideneamino)-2,4,6-triiodobenzoyl]-β-amino-α-methylpropionitrile, that is to say 93.6% of theory, are obtained.

EXAMPLE 7

137 g of the N-[3-(1'-3''-oxapentamethyleneamino-ethylideneamino)-2,4,6-triiodobenzoyl]-β-amino-α-methylpropionitrile obtained in the preceding examples are dissolved in 300 ml of concentrated hydrochloric acid and the solution is heated to 80° C. After 2 hours, the hydrolysis has ended and the aqueous-hydrochloric acid solution is evaporated in vacuo. The residue is dissolved in aqueous sodium hydroxide solution and insoluble constituents are filtered off. The acid is precipitated from the filtrate by adjusting the pH value to 4.5. 123 g (87.6% of theory) of N-[3-(1'-2''-oxapentamethyleneamino-ethylideneamino)-2,4,6-triiodobenzoyl]-β-amino-α-methylpropionic acid are obtained. A further 16.2 g of acid (11.5%) are obtained by concentrating the mother liquor. After recrystallizing the combined products from methanol, 124 g of pure crystalline acid of melting point: 202°–205° C. are obtained, that is to say 87.2% of theory, relative to N-(3-amino-2,4,6-triiodobenzoyl)-β-amino-α-methylpropionitrile, if the preparation procedure according to Example 1 was used for the preparation of the nitrile.

EXAMPLE 8

34.5 g of N-[3-(1'-3''-oxapentamethyleneamino-ethylideneamino)-2,4,6-triiodobenzoyl]-β-amino-α-methylpropionitrile are dissolved in 1 l of hot 96% strength alcohol and, after adding 20 g of 20% strength sodium hydroxide solution, the mixture is boiled under reflux for 2 hours. The alcohol is then stripped off and the residue is diluted with water to 500 ml and adjusted to pH 1 with hydrochloric acid. The flakes which thereby separate out are filtered off. The acid is precipitated from the clear filtrate by adjusting the pH to 4.5, and is filtered off. After recrystallizing from methanol, 25 g of pure crystalline N-[3-(1'-3''-oxapentamethyleneamino-ethylideneamino)-2,4,6-triiodobenzoyl]-β-amino-α-methylpropionic acid of melting point: 202°–205° C. are obtained, that is to say 72% of theory, relative to N-(3-amino-2,4,6-triiodobenzoyl)-β-amino-α-methylpropionitrile if the preparation of the nitrile was carried out according to Example 1.

EXAMPLE 9

30 g of N-[3-(1'-3''-oxapentamethyleneamino-ethylideneamino)-2,4,6-triiodobenzoyl]-β-amino-α-methylpropionitrile are boiled under reflux in 150 ml of 10 N methanolic HCl for 2 hours. All the methanolic hydrochloric acid is distilled off, the evaporation residue is taken up in 300 ml of water, the aqueous mixture is boiled up for a short time and insoluble constituents are filtered off. The acid is precipitated by adjusting the pH value to 4.5, and is isolated. After recrystallizing from methanol, 24.2 g of N-[3-(1'-3''-oxapentamethyleneamino-ethylideneamino)-2,4,6-triiodobenzoyl]-β-amino-α-methylpropionic acid of melting point: 202°–205° C. are obtained. The yield is 78% of theory, relative to N-(3-amino-2,4,6-triiodobenzoyl)-β-amino-α-methylpropionitrile, on the basis of the preparation of the nitrile in accordance with the method of Example 1.

What we claim is:
1. N-[3-(1'-3''-Oxapentamethyleneamino-ethylideneamino)-2,4,6-triiodobenzoyl]-β-amino-α-methyl-propionitrile.

* * * * *